United States Patent
Oyama et al.

(10) Patent No.: US 6,663,623 B1
(45) Date of Patent: Dec. 16, 2003

(54) ELECTRIC SURGICAL OPERATION APPARATUS

(75) Inventors: Masahide Oyama, Hino (JP); Kenji Harano, Hachioji (JP); Hiroyuki Takahashi, Akishima (JP); Kazuya Hijii, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/524,336

(22) Filed: Mar. 13, 2000

(51) Int. Cl.$^7$ ............................................. A61B 18/18
(52) U.S. Cl. ............................. 606/38; 606/37; 606/42
(58) Field of Search ........................... 606/32, 33, 34, 606/38, 91, 37, 42, 45, 48–50; 128/898

(56) References Cited

U.S. PATENT DOCUMENTS

| | | | |
|---|---|---|---|
| 4,727,874 A | | 3/1988 | Bowers et al. |
| 5,496,312 A | * | 3/1996 | Klicek .......................... 606/49 |
| 5,743,903 A | * | 4/1998 | Stern et al. ..................... 606/42 |
| 5,827,271 A | | 10/1998 | Buysse et al. |
| 5,931,836 A | * | 8/1999 | Hatta et al. ..................... 606/38 |
| 6,022,347 A | * | 2/2000 | Lindenmeier et al. ......... 606/38 |
| 6,139,546 A | * | 10/2000 | Koenig et al. ................. 606/34 |
| 6,293,942 B1 | * | 9/2001 | Goble et al. ................... 606/38 |
| 6,306,131 B1 | * | 10/2001 | Hareyama et al. ............. 606/38 |
| 6,309,386 B1 | * | 10/2001 | Bek ............................... 606/34 |

FOREIGN PATENT DOCUMENTS

| | | |
|---|---|---|
| JP | 61-124266 | 6/1986 |
| JP | 07-213530 | 8/1995 |
| JP | 9-066058 A | 3/1997 |
| JP | 10-510460 | 10/1998 |
| JP | 2000-500356 A | 1/2000 |

OTHER PUBLICATIONS

Japanese Office Action mailed Apr. 8, 2003 issued in a counterpart Japanese Patent Application No. 1998–215415, and English translation thereof.

* cited by examiner

Primary Examiner—John Mulcahy
Assistant Examiner—David M. Ruddy
(74) Attorney, Agent, or Firm—Frishauf, Holtz, Goodman & Chick, P.C.

(57) ABSTRACT

The electric surgical operation apparatus of the present invention easily and securely shortens the rising time until incision and coagulation effects appear even if electrodes having different volumes or surface areas are used for the treatment tool. Cutting sharpness and safety are improved and the operation time is shortened. In the electric surgical operation apparatus, contact of a monopolar electrode of a monopolar treatment tool with organic tissue is detected by a voltage or current sensor. Based on a detection signal therefrom, a high-frequency output is supplied at a predetermined value from a high-frequency cautery power source device, and a high-frequency output is supplied at a higher initial setting value than the predetermined value during an initial period at a rising time. Setting of at least one of the initial period and the initial setting value can be changed.

24 Claims, 14 Drawing Sheets

| SETTING OUTPUT | DUTY TO CONTROL SIGNAL | AMPLIFIER SUPPLY VOLTAGE |
|---|---|---|
| 50W | 12.5% | 30V |
| 100W | 12.5% | 60V |
| 150W | 12.5% | 90V |
| 200W | 25.0% | 60V |
| 250W | 25.0% | 75V |
| 300W | 25.0% | 90V |

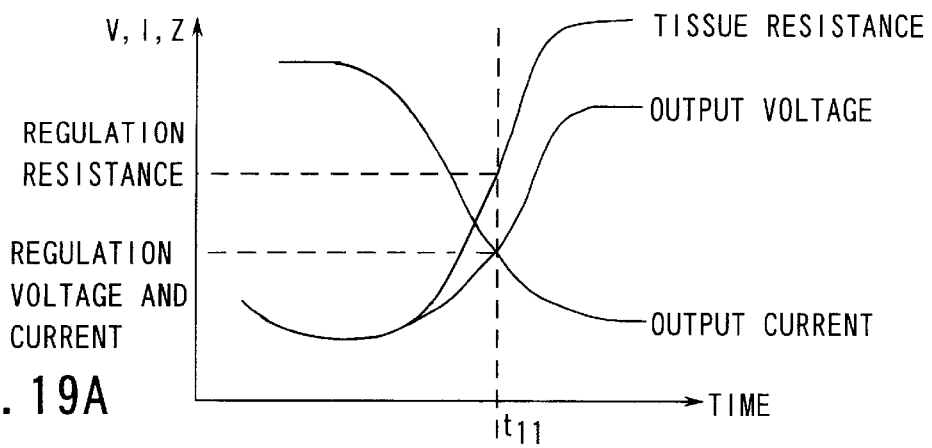
FIG. 19A
FIG. 19B
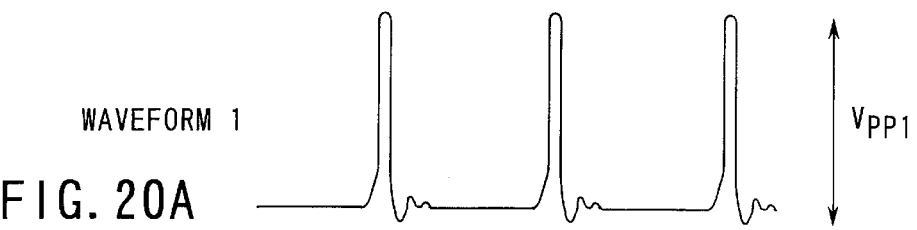
FIG. 20A
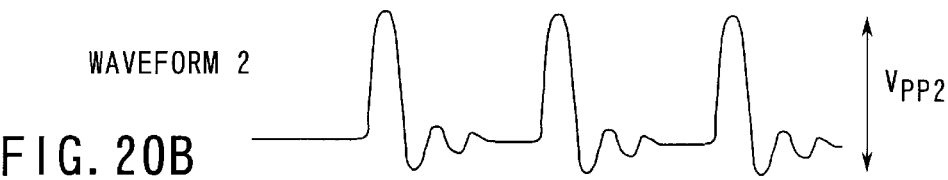
FIG. 20B
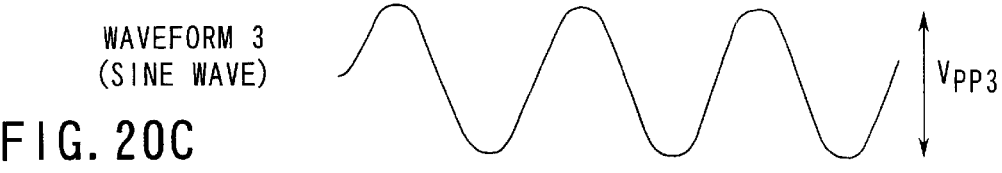
FIG. 20C

ELECTRIC SURGICAL OPERATION APPARATUS

BACKGROUND OF THE INVENTION

The present invention relates to an electric surgical operation apparatus and more specifically to an electric surgical operation apparatus which lets a high-frequency current flow through organic tissue to make treatments such as cutting, coagulation, and the like of organic tissue by heat generated by the high-frequency current.

An electric surgical operation apparatus is used generally in surgical operations to make treatments such as cutting, coagulation or the like on organic tissue by letting a high-frequency current flow through organic tissue. This kind of electric surgical operation apparatus comprises an electric surgical operation apparatus body, a treatment tool having an active electrode, and a feedback electrode which is let contact the body surface of a patient.

Further, a high-frequency power is generated from the electric surgical operation apparatus body, and the active electrode is brought into contact with a treating portion to let a high-frequency current concentrically through organic tissue. The high-frequency current is collected diffusely by the feedback electrode, and treatments such as cutting, coagulation, and the like of organic tissue can thereby be achieved.

In this kind of electric surgical operation apparatus, the time from turning-on of an output switch to appearance of a cutting or coagulation effect (which will be hereinafter called a rising time) is shortened to improve sharpness of cutting, shortening of the treating time, and the safety. That is, in a conventional apparatus as shown in FIG. 1, to shorten the rising time, a larger power (e.g., $P_0$) than a setting value (e.g., 30 W) is supplied for a predetermined time period by a time point $t_0$ when a fixed delay time has elapsed after a time point when an output switch was turned on, and the setting power is supplied after the time point $t_0$.

Meanwhile, in an electric surgical operation apparatus, various kinds of active electrodes to be provided at the top ends of the treatment tools are prepared in compliance with applications. FIGS. 2A, 2B and 2C show examples of active electrodes, more precisely a loop electrode a band electrode and a grooved roller electrode.

These electrodes have different volumes depending on their shapes. Therefore, even if an equal high-frequency current is supplied from an electric surgical operation apparatus body, the current density differs between electrodes, at the treating portion. That is, if an equal high-frequency current is used, a loop electrode 2 having a small volume attains the highest current density (which means that heat is easily generated), and a band electrode 4 and a grooved roller electrode 6 respectively attain the second and third highest current densities.

Then, as shown in FIG. 3, if an equal high-frequency power is used, the resistance of tissue rises in different ways among the loop electrode shown at a in the figure, the band electrode at b, and the grooved roller electrode at c, thereby causing differences. As a result of this, as described previously, for example, the loop electrode 2 may generate heat sufficient to achieve performance (e.g., denaturation of organic tissue) while the grooved roller electrode 6 cannot generate enough heat to attain sufficient performance, if a larger power than a present value is supplied for a predetermined time period after the output switch is turned on in order to hasten the rising.

Also, Japanese Patent Application KOKAI Publication No. 9-56725 discloses a high-frequency electronic knife apparatus which comprises an operation panel, a control circuit for controlling the entire apparatus based on the contents of an operation through the operation panel, a waveform generator circuit for generating a waveform corresponding to an output mode by receiving a waveform selection signal corresponding to the output mode from the control circuit, a switching circuit which is driven and turned on/off according to the waveform from the waveform control circuit, a variable power source circuit which generates a DC (direct current) power set under control by the control circuit, and a resonance circuit which causes the DC power of the variable power source circuit to resonate by driving the switching circuit thereby to generate a high-frequency power, wherein the control circuit controls the output timing of the high-frequency waveform from the waveform generator circuit.

In the high-frequency electric knife apparatus described in the above publication No. 9-56725, various outputs can be obtained by changing the drive waveform for the switching circuit. Also, the control signal for a switching element of the resonance circuit is switched merely according to the output mode but does not depend on the status of loads.

Meanwhile, the waveforms generated by the waveform generator circuit, e.g., the waveforms in a cutting mode, mixed mode, and coagulation mode use signals having fixed duties. In view of construction of the resonance circuit, for example, if switching is sequentially carried out as in the cutting mode and if the duty is fixed, the voltage supplied to the resonance circuit must be increased to increase the output.

However, if the control signal for switching has a small duty as in the high-frequency electric knife apparatus described in the above publication No. 9-56725, the power source supplied to the resonance circuit requires a power source of a considerably high voltage. A problem hence appears in that the power source must have a large size so that the apparatus itself also must have a large size or an expensive power source is required. In addition, if the supplied voltage is high, there is a problem that a high-frequency leakage current is caused.

Further, Japanese Patent Application KOKAI Publication No. 7-79996 discloses a tissue cutting apparatus comprising a source which supplies cutting energy, an electrode means which is connected to the supply source and discharges energy at a cutting voltage, a current monitor means which measures a current transferred to the electrode means and generates a measured current signal, a voltage monitor means which measures a voltage in the electrode means and generates a measured voltage signal, and a control means which performs predetermined functions based on measured tissue impedance.

This tissue cutting apparatus measures a current transferred to the electrode part and generates a measured current signal. This apparatus also measures a voltage at the electrode part and generates a measured voltage signal. Further, the measured voltage signal is divided by the measured current signal, to obtain a measured tissue impedance signal.

The tissue cutting apparatus described in the above publication No. 7-79996 includes a current sensor and a voltage sensor and further requires an calculation circuit for dividing a measured voltage signal by a measured current signal. Also, in this kind of tissue cutting apparatus or an electric surgical operation apparatus, a treatment on tissue is completed normally in a short time period of several tens to several hundreds sec., and therefore, a high-speed calculation circuit is required.

Meanwhile, necessities for a sensor and a calculation circuit as described above result in a complicated structure of the apparatus and increase of costs.

BRIEF SUMMARY OF THE INVENTION

Hence, the present invention has an object of providing an electric surgical operation apparatus capable of easily and securely shortening the rising time required till a cutting effect and a coagulation effect appear so that the cutting sharpness is improve, the operation time is shortened, and the safety is improved, without complicating the structure of the apparatus or increasing costs, even if electrodes having different volumes or different surface areas are used for an operation tool.

That is, a first object of the present invention is to provide an electric surgical operation apparatus comprising: treatment means for contacting an organism to make a treatment thereon; detection means for detecting contact of the treatment means with the organism; first output means for supplying a high-frequency output at a predetermined value, based on a signal detected by the detection means; and second output means for supplying a high-frequency output at a higher initial setting value than the predetermined value at an initial period in a rising time, wherein the second output means can change setting of at least one of the initial period and the initial setting value.

A second object of the present invention is to provide an electric surgical operation apparatus comprising: first means for determining whether or not an electrode of a treatment tool contacts tissue of an organism; second means for setting a larger initial output than a predetermined setting output during a predetermined period at a rising time if the electrode of the treatment tool is determined as contacting the tissue of the organism; third means for taking in information concerning the tissue of the organism; fourth means for determining whether or not the information concerning the tissue taken in by the third means is equal to or more than a regulation value; and fifth means for changing the initial output to the predetermined setting output if the information concerning the tissue taken in by the fourth means is equal to or more than the regulation value.

A third object of the present invention is to provide an electric surgical operation apparatus which cuts and coagulate organic tissue by a high-frequency power, comprising: high-frequency power generation means for generating the high-frequency power by switching a direct current power by a high-frequency pulse, thereby to generate the high-frequency power; setting means for setting the high-frequency power generated by the high-frequency power generation means, to a predetermined setting output; pulse generation means for generating the high-frequency pulse; and control means for outputting a control signal to instruct generation of the high-frequency pulse, to the pulse generation means, wherein the control means changes a duty to the high-frequency pulse in accordance with a setting output set by the setting means.

A fourth object of the present invention is to provide an electric surgical operation apparatus which cuts and coagulate organic tissue by a high-frequency power, comprising: high-frequency power generation means for generating the high-frequency power by switching a direct current power by a high-frequency pulse, thereby to generate the high-frequency power; pulse generation means for generating the high-frequency pulse; condition detection means for detecting a condition of the organic tissue thereby to output a condition detection signal; control means for changing a duty to the high-frequency pulse in accordance with the condition detection signal outputted from the condition detection means and for outputting a control signal to instruct the pulse generation means about generation of the high-frequency pulse, in accordance with a change of the duty.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 11A and 11B explain a second embodiment of the present invention, wherein FIG. 11A is a characteristic graph showing a time-based change of a tissue resistance or a voltage and FIG. 11B is a characteristic graph showing a time-based change of an actual output of a treatment tool.

FIGS. 12A and 12B explain a third embodiment of the present invention, wherein FIG. 12A is a characteristic graph showing a change rate of tissue resistance or voltage, and FIG. 12B is a characteristic graph showing a time-based change of an actual output of a treatment tool.

FIGS. 19A and 19B explain feedback control, wherein FIG. 19A is a characteristic graph showing time-based changes of the voltage applied to organic tissue, the current, and the resistance of tissue and FIG. 19B is a characteristic graph showing a time-based change of an actually supplied power.

FIGS. 20A through 20C shows waveforms of output voltages, wherein FIG. 20A shows a waveform 1 at a peak value $V_{PP1}$, FIG. 20B shows a waveform 2 at a peak value $V_{PP2}$ having higher tissue impedance than the waveform 1, and FIG. 20C shows a waveform 3 at a peak value $V_{PP3}$ having much higher tissue impedance than the waveform 2.

DETAILED DESCRIPTION OF THE INVENTION

In the following, embodiments of the present invention will be explained with reference to the drawings.

Figure 4:
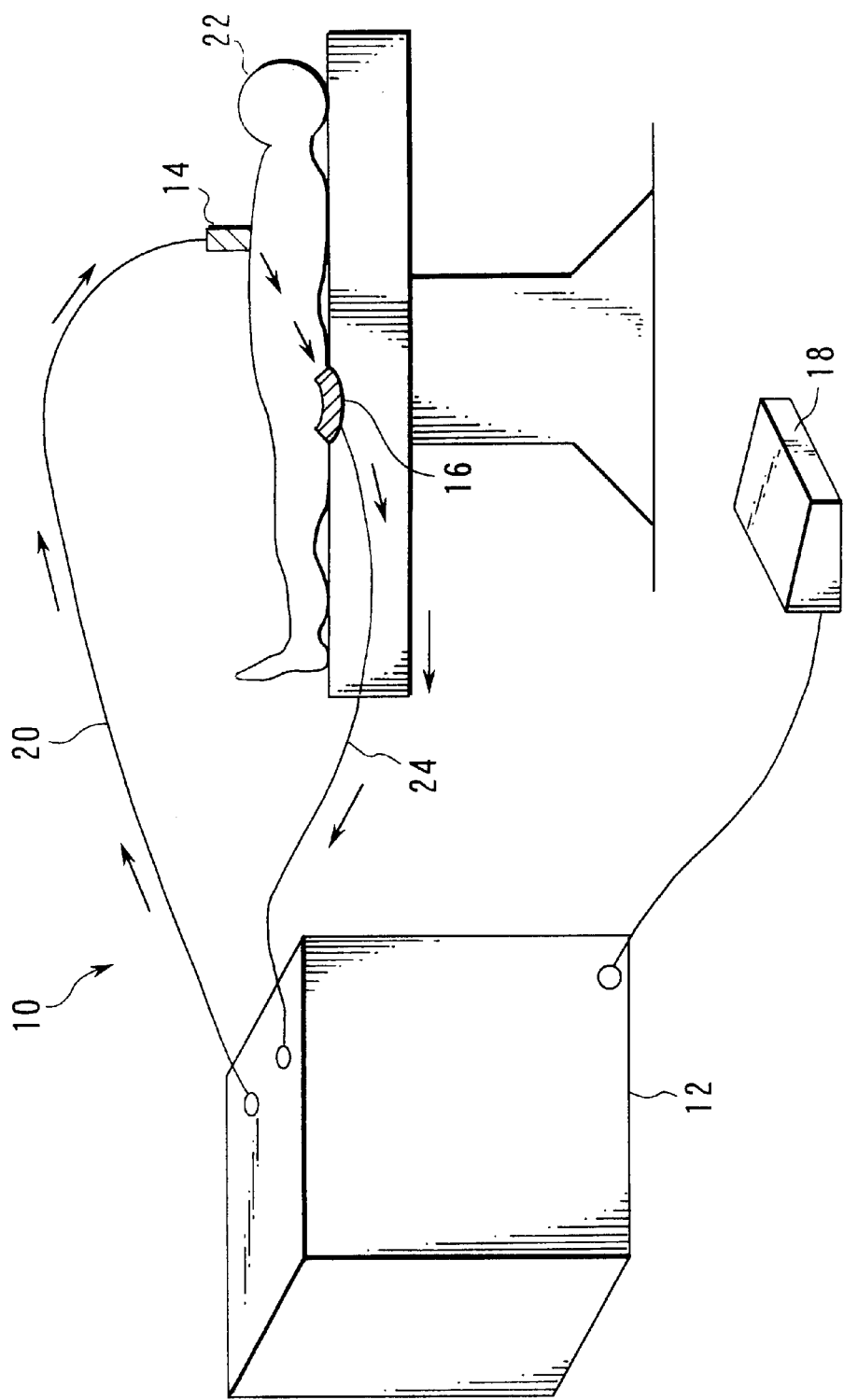
FIG. 4 is a view illustrating a schematic structure of an electric surgical operation apparatus according to the first embodiment of the present invention.

FIG. 4 is a view illustrating the schematic structure of an electric surgical operation apparatus according to a first embodiment of the present invention.

In FIG. 4, the electric surgical operation apparatus 10 is comprised of a high-frequency cautery power source device 12, a monopolar electrode 14, a feedback electrode 16, and a foot switch 18.

The monopolar electrode 14 has an active electrode which is connected through a code 20 of an active line to make a treatment on a treating portion of a patient 22. The monopolar electrode 14 has a top end whose cross-section is constructed as a very narrow area so that a current is concentrated to generate heat by which a treatment is made.

The feedback electrode 16 contacts the body surface of the patient 22 and is connected with a feedback cord 24. The feedback electrode 16 is constructed to have a sufficiently wide area so that the body surface of the patient 22 might not be burnt.

In this structure, when the foot switch 18 is turned on, the high-frequency cautery power source device 12 is started. Further, a high-frequency power is generated as an energy source by the high-frequency cautery power source device 12. The active electrode of the monopolar treatment tool 14 is then let contact a treating portion of the patient 22, and a high-frequency current is let flow concentrically into organic tissue. Further, the high-frequency current is diffusively collected through the feedback electrode 16, and thus, a treatment such as cutting, coagulation, or the like is carried out for the treating portion.

Although not shown in the figure, the monopolar treatment tool 14 may be provided with a switch similar to the foot switch 18, in place of using the foot switch 18.

Figure 5A:
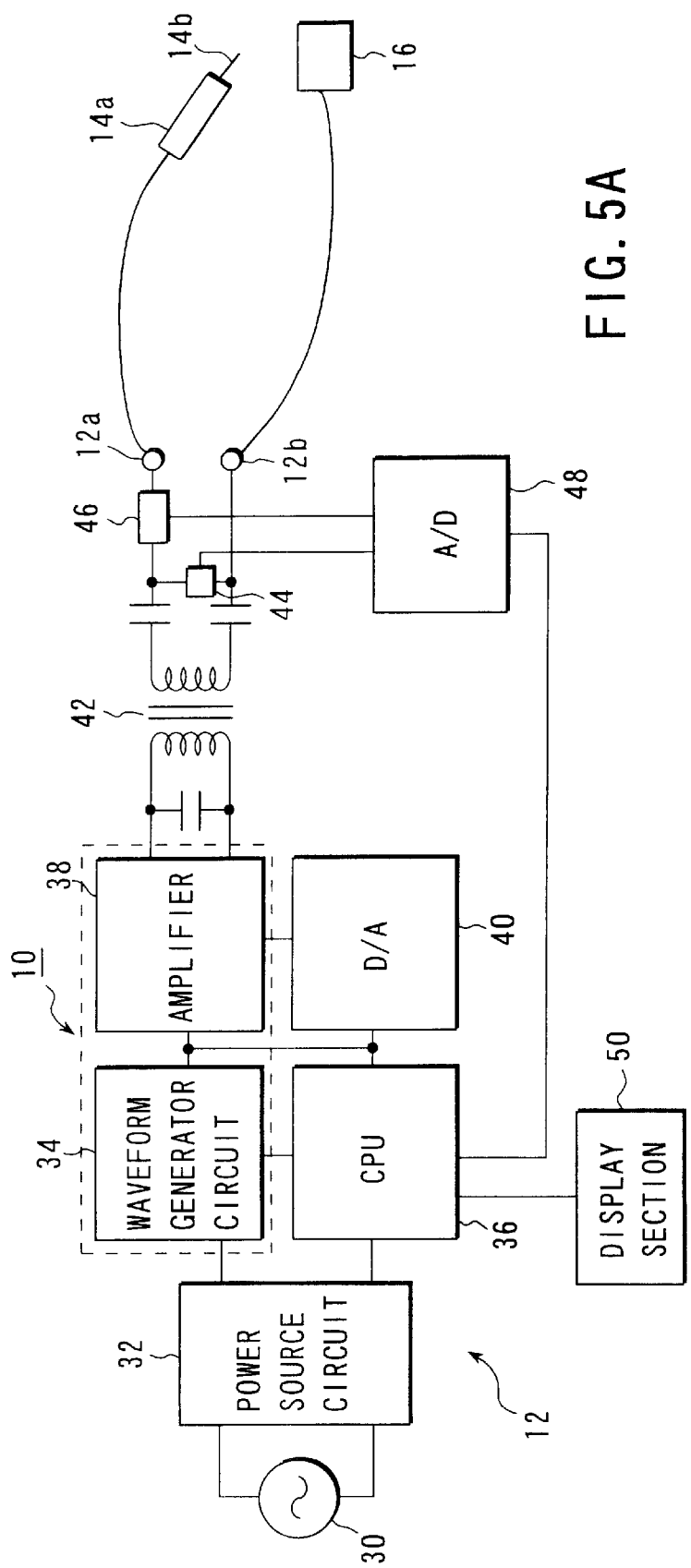
FIG. 5A is a diagram showing an internal structure of a high-frequency cautery power source device.
Figure 5B:
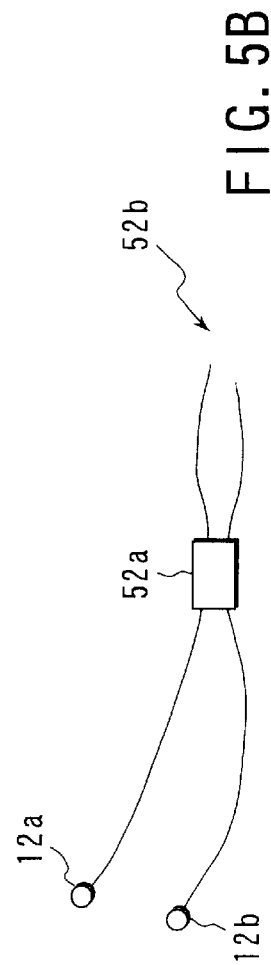
FIG. 5B is a view showing the structure of a bipolar treatment tool.

FIG. 5A shows an internal structure of the high-frequency cautery power source device 12.

In FIG. 5A, a commercial power source 30 is connected with a power source circuit 32 for supplying a desired supply voltage. Further, this power source circuit 32 is connected with a waveform generator circuit 34 for generating a waveform corresponding to an output mode depending on the contents of an operation, and with a CPU 36 for controlling the entire apparatus of the high-frequency cautery power source device 12. The waveform generator circuit 34 and the CPU 36 are connected with a D/A converter 40 for converting a digital signal from the CPU 36 into an analogue signal to control an amplifier 38, and with the amplifier 38 for amplifying a very weak signal obtained by the waveform generator circuit 34.

An output transformer 42 is connected, in its primary side, with the amplifier 38, and is also connected, in its secondary side, with capacitors and terminals 12a and 12b through a voltage sensor 44 and a current sensor 46. Signals detected by the voltage sensor 44 and the current sensor 46 are converted into digital signals by the A/D converter 48 and outputted to the CPU 36. Also, the CPU 36 is connected with a display section 50.

The terminal 12a is connected to a monopolar treatment tool 14a and a monopolar electrode 14b through active lines. Meanwhile, the terminal 12b is connected to the feedback electrode 16 though a feedback line.

Figure 1:
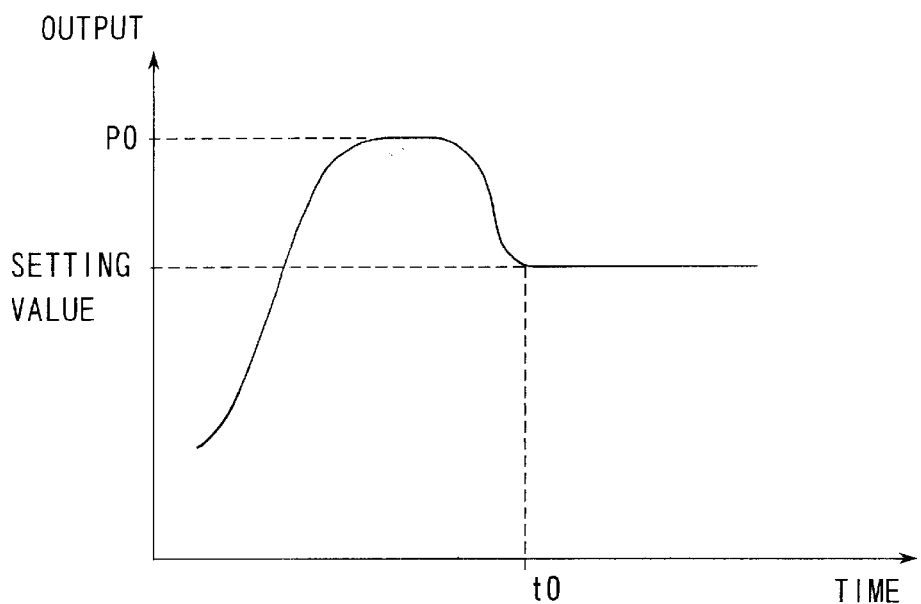
FIG. 1 is a graph which explains an effect of a conventional electric surgical operation apparatus.
Figure 2A:
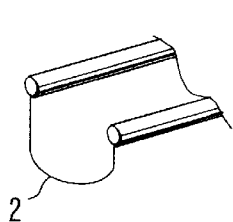
FIGS. 2A through 2C shows examples of active electrodes wherein FIG. 2A show a loop electrode, FIG. 2B show a band electrode, and FIG. 2C show, a grooved roller electrode.
Figure 2B:
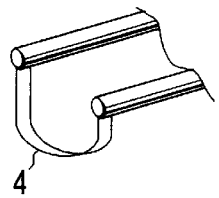
Figure 2C:
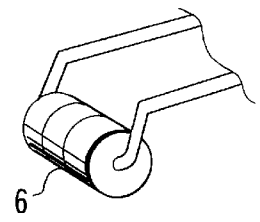
Figure 3:
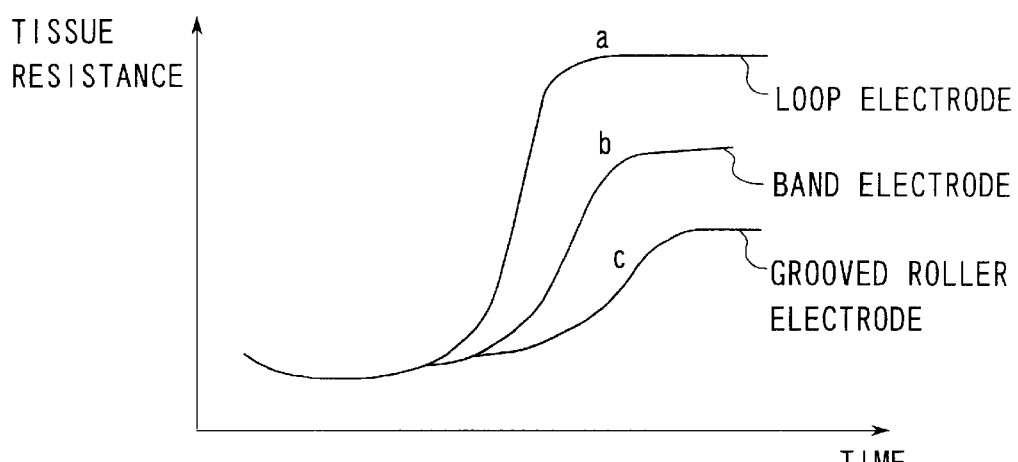
FIG. 3 is a graph showing a relationship between the shape of electrode of the electric surgical operation apparatus and tissue resistance.

Although FIG. 2A shows a monopolar treatment tool as a treatment tool, it is possible to use a bipolar treatment tool 52a and a bipolar electrode 52b as shown in FIG. 2B. In this case, the feedback electrode 16 is unnecessary.

As has been already described with respect to the prior art, electrodes of a treatment tool provide different current densities depending on the shapes of the electrodes even if an equal high-frequency power is supplied. Therefore, to attain a sufficient performance with every electrode, for example, a band electrode or a grooved roller electrode, which has a large volume and therefore generates less heat, should be arranged so as to generate sufficient heat, with respect to a loop electrode having a small volume.

To attain such a performance, it is necessary that the heat generation amount of the treatment tool be constant independently from the shapes of the electrodes. That is, when a high-frequency power (which will be hereinafter called an initial power) higher by a regulation output than a setting power is obtained for a regulation time period after the output switch is turned on and a contact between organic tissue and the electrode is detected, the initial output of the band electrode or the grooved roller electrode is set to be high relatively to the initial output of the loop electrode. Otherwise, the duration time of the initial output of the band electrode or the grooved roller electrode is set long relatively to that of the loop electrode.

For example, in case of setting the initial outputs, the initial output of the loop electrode is set 1.5 times higher than a setting output, the band electrode 2.5 times, as well as that of the grooved roller electrode 3 times. Also, in case of setting the duration time periods of the initial outputs, the duration time period of the loop electrode is set to 10 ms, that of the band electrode to 20 ms, as well as that of the roller electrode to 30 ms.

Explained next will be specific examples of setting of the heat generation amount in the treatment tool as described above.

Figure 6:
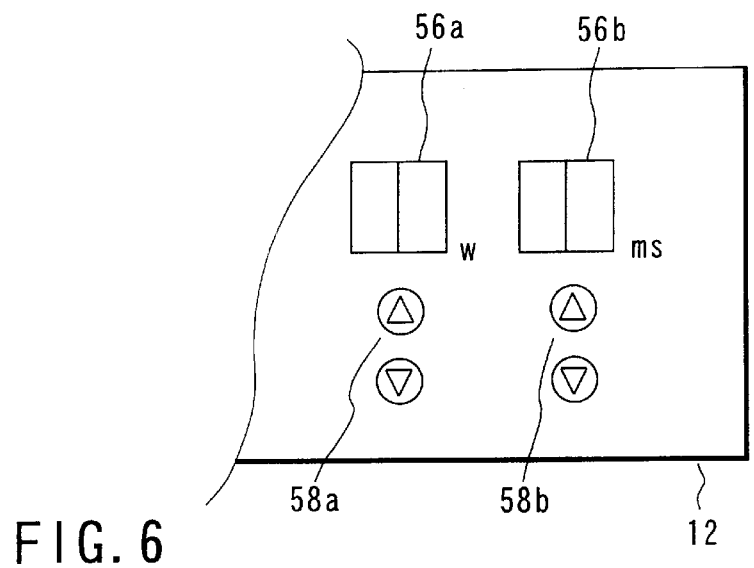
FIG. 6 is a view showing an example of a display section provided on a front panel of the high-frequency cautery power source device.

FIG. 6 is a view showing an example of a display section provided on the front panel of the high-frequency cautery power source device 12.

In FIG. 6, on the front panel of the high-frequency cautery power source device 12, there are provided an output display section 56a which indicates a output value which is higher than the setting output during a rising time, i.e., the numerical value of the initial output, and a time display section 56b which indicates a time for which the initial output should be continued. Setting keys 58a and 58b by which a user previously sets an output value and a time are provided below the output display section 56a and the time display section 56b.

A user operates the setting keys 58a and 58b in correspondence with the shape of the electrode to be used as a monopolar electrode, to set the numerical value of the initial output or the duration time of the initial output. For example, the output values of the band electrode and the grooved roller electrode are set higher compared with the output value of the loop electrode. Otherwise, the duration time periods of the band electrode and the grooved roller electrode are set longer compared with the duration time period of the loop electrode.

By this setting, sufficient heat generation can be attained and excellent performance can be obtained even if the treatment tool uses an electrode of any shape.

Figure 7:
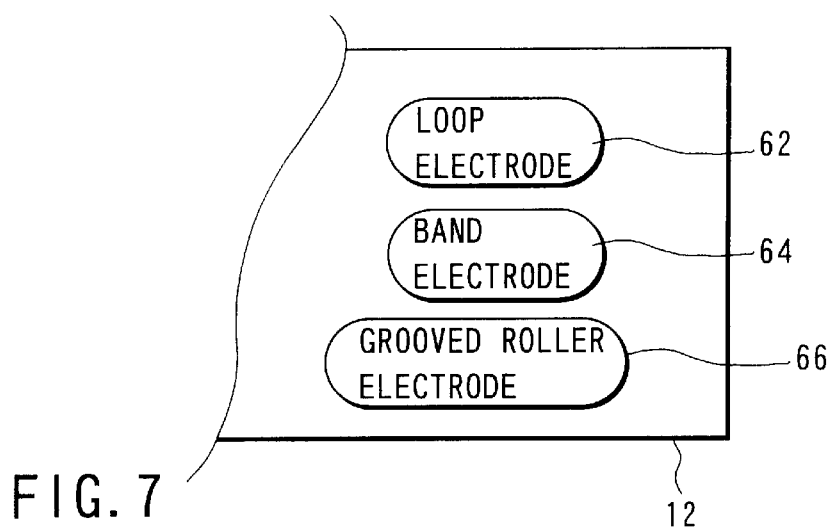
FIG. 7 is a view showing another example of the display section.

FIG. 7 is a view showing another example of the display section.

In FIG. 7, on the front panel of the high-frequency cautery power source device 12, there are provided a loop electrode select key 62, a band electrode select key 64, and a grooved roller electrode select key 66. These select keys 62, 64, and 66 enable selection of outputs at the rising time or output duration time periods at the rising time respectively corresponding to the shapes of electrodes.

That is, the user presses down any of the loop electrode select key 62, band electrode select key 64, and grooved roller electrode select key 66 in correspondence with the shape of the electrode to be used as a monopolar electrode. In this manner, for example, the value of the initial output at the rising time in case of operating the band electrode select key 64 or the grooved roller electrode select key 66 is set higher or the duration time period of the initial output is set longer, compared with the case of operating the loop electrode select key 62.

By this setting, sufficient heat generation can be attained and excellent performance can be obtained even if the treatment tool uses an electrode of any shape. In addition, the output value and the duration time period may be set in combination with each other, e.g., the setting may be arranged such that the output value is higher and the output duration time period is longer.

In the example shown in FIGS. 6 and 7, a user operates the operation panel to set an initial output or a duration time period of the initial output. However, the present embodiment is not limited hitherto but a means for automatically distinguishing the electrode may be provided for the connector of the treatment tool.

Figure 8:
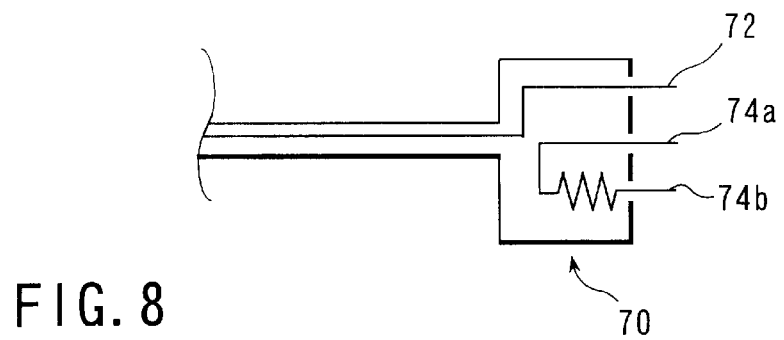
FIG. 8 is a view showing a structural example of a connector for detecting the shape of a monopolar electrode.

FIG. 8 is a view showing a structural example of a connector for detecting the shape of a monopolar electrode.

In FIG. 8, the connector 70 comprises an active line 72, and identification pins 74a and 74b which are connected with each other through a resistor. If this connector 70 is connected to the body of the high-frequency cautery power source device 12, for example, a detection current flows from the body to the identification pins 74a and 74b. Which of a loop electrode, band electrode, and grooved roller electrode the treatment tool has is determined by a voltage which is generated between both ends of the identification pins 74a and 74b.

By this structure, the type of the electrode of treatment tool is automatically distinguished, so an optimum initial output value and optimum duration time can be automatically set for each electrode. Excellent performance can be attained even if any electrode is used.

Figure 9:
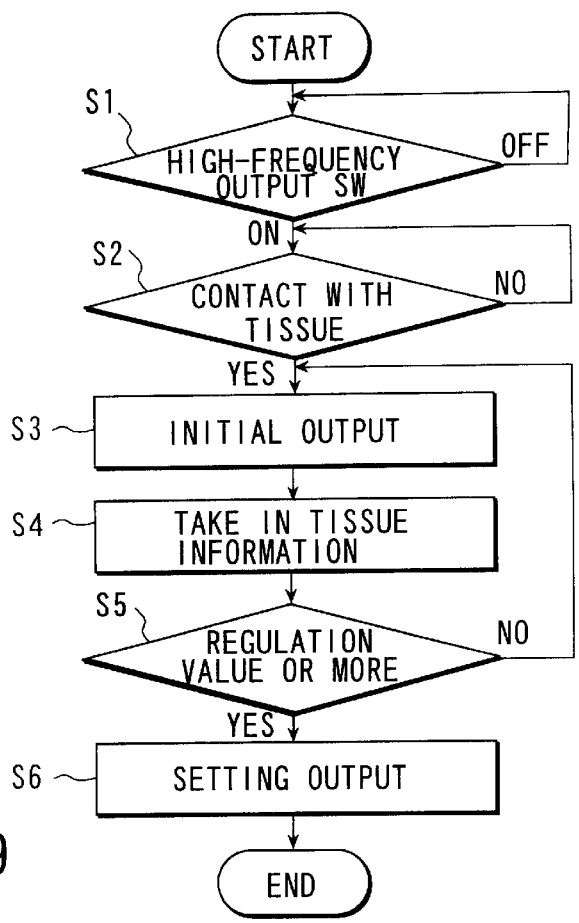
FIG. 9 is a flowchart which explains the operation of the first embodiment.

FIG. 9 is a flowchart which explains the operation of the first embodiment described above.

At first, in a step S1, whether or not a switch for a high-frequency output which is the foot switch 18 is on is determined. If the foot switch 18 is on, whether or not the electrode of the treatment tool has contacted organic tissue is determined in a subsequent step S2. In this case, the voltage sensor 44 and the current sensor 46 determine whether or not the electrode is in contact with tissue.

If the electrode is in contact with tissue, the flow to a step S3 where an initial output is set. The initial output is a high-frequency output which is outputted for a regulation time period at the rising time at a higher value than that of a setting output. Next, in a step S4, tissue information is taken in. The tissue information means a voltage applied to a load, impedance of tissue, a current flowing through tissue, and the like and is taken in by the voltage sensor 44, the current sensor 46, and the like.

Further, in a step S5, whether or not the tissue information thus taken in is equal to or more than a regulation value is determined. If the tissue information does not reach a regulation value, the flow returns to the steps S3 and the processing in the steps subsequent thereto are repeated. Meanwhile, if the tissue information is equal to or more than a regulation value, the flow goes to a step S6 and the output is reduced to the setting output.

Further, the following will be an example of automatically distinguishing the type of an electrode of a treatment tool.

Figure 10:
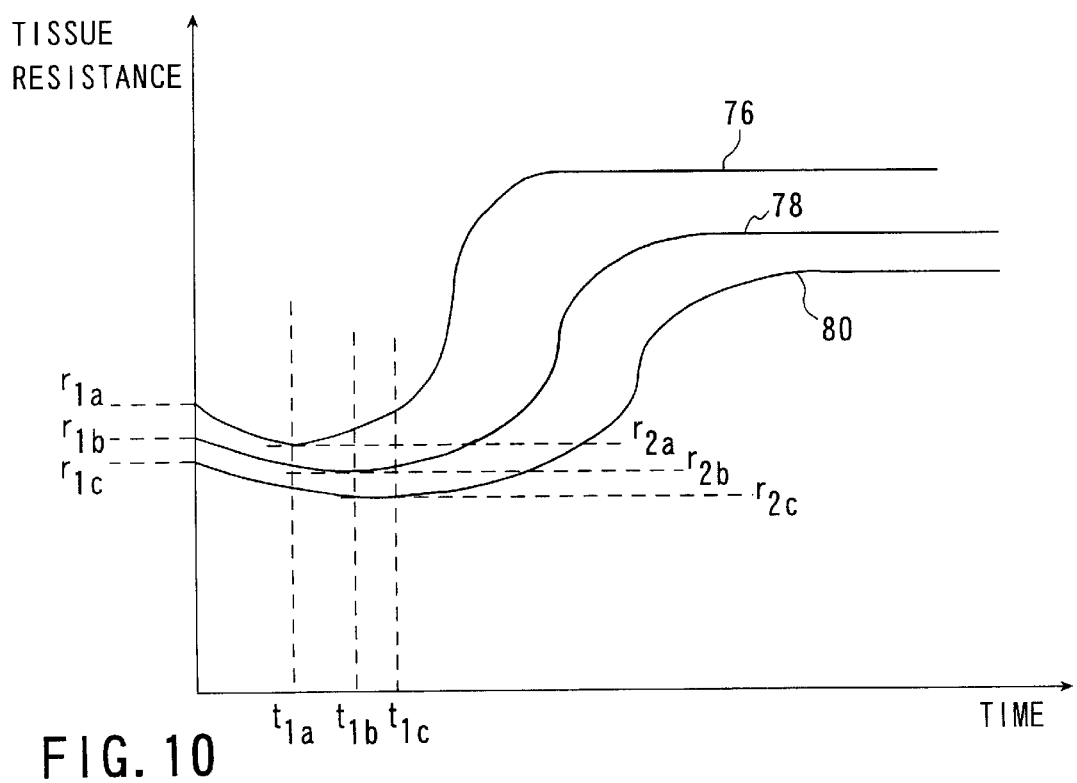
FIG. 10 is a graph showing the relationship between each electrode and tissue resistance for determining the shape of the electrode of the electric surgical operation apparatus.

FIG. 10 is a graph showing relationships between electrodes and tissue resistances for determining the shape of electrodes of an electric surgical operation apparatus. In the figure, the reference 76 indicates a characteristic curve of the tissue resistance with respect to a loop electrode, the reference 78 with respect to a band electrode, as well as the reference 80 with respect to a grooved roller electrode.

Further, as examples of determining each of the electrodes, there are methods in which the type of an electrode is distinguished depending on the value of the tissue resistance. For example, in the first one of those methods, an electrode is determined as a loop electrode 76 if the initial value of the tissue resistance is a value expressed as $r_{1a}$. If the initial value is $r_{1b}$, the electrode is a band electrode 78. If the initial value is $r_{1c}$, the electrode is a grooved roller electrode 80.

In the second method, the type of the electrode is determined depending on the time until the tissue resistance becomes a minimum value. For example, if it takes a time $t_{1a}$ till the tissue resistance becomes a minimum value, the electrode is determined as a loop electrode 76. If it takes a time $t_{1b}$, the electrode is a band electrode 78. If it takes a time $t_{1c}$, the electrode is a grooved roller electrode 80.

Further, in the third method, the type of the electrode is determined depending on the lowermost value of the tissue resistance. That is, after each electrode is rendered electrically conductive, the tissue resistance once decreases and then increases. The type of the electrode hence can be determined.

For example, if the lowermost value of the tissue resistance is a value expressed as $r_{2a}$, the electrode is a loop electrode 76. If it is a value expressed as $r_{2b}$, the electrode is a band electrode 78. If it is a value expressed as $r_{2c}$, the electrode is determined as a grooved roller electrode 80.

The three methods may be used in any possible combination to determine the type of the electrode more accurately. It is thus possible to determine automatically the electrode of the treatment tool depending on the tissue resistance.

Next explanation will be made of a second embodiment.

In the embodiment described below, the same elements as those described above will be denoted by the same reference symbols and detailed explanation thereof will be omitted herefrom.

Figure 11A:
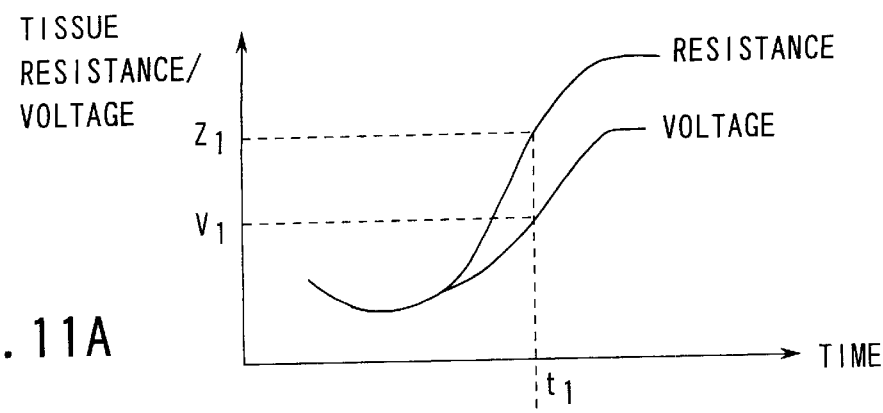
Figure 11B:
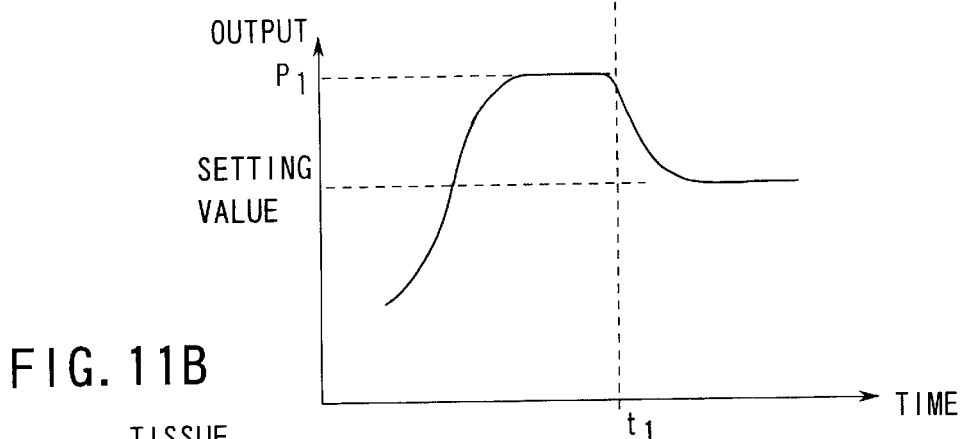

FIG. 11A is a characteristic graph showing a time-based change of a tissue resistance or a voltage. FIG. 11B is a characteristic graph showing a time-based change of an actual output of the treatment tool.

After the output switch is turned, the high-frequency output increases and reaches a preset initial output value $P_1$. The tissue resistance and the voltage then increase. Further, it is detected that a preset resistance value $Z_1$ and a preset voltage value $Z_1$ have been reached, by monitoring from the voltage sensor 44. At this time point (time $t_1$), stable cutting is enabled by the treatment tool. After the time $t_1$ has passed, the output of the treatment tool is reduced from the initial output value $P_1$ to a normal setting value.

Thus, the electrode of the treatment tool can be distinguished by determining the time period from when the output switch is turned on to when the resistance value $Z_1$ and the voltage value $V_1$ which have been previously set are obtained. That is, in case of an electrode which less generates heat, a longer time is required till the resistance value $Z_1$ and the voltage value $V_1$ are reached. Therefore, by comparing the cutting-enable time point $t_1$ between electrodes, the type of each electrode can be identified. For example, the loop electrode has the earliest cutting-enable time point $t_1$, the band electrode has the second earliest time point $t_1$, and the grooved roller electrode has the third earliest time point $t_1$.

A third embodiment of the present invention will be explained next.

In the second embodiment described above, the cutting-enable time is detected by absolute values, i.e., a tissue resistance value and a voltage value which are preset. In contrast, the third embodiment operates to detect change rates of the tissue resistance and the voltage.

Figure 12A:
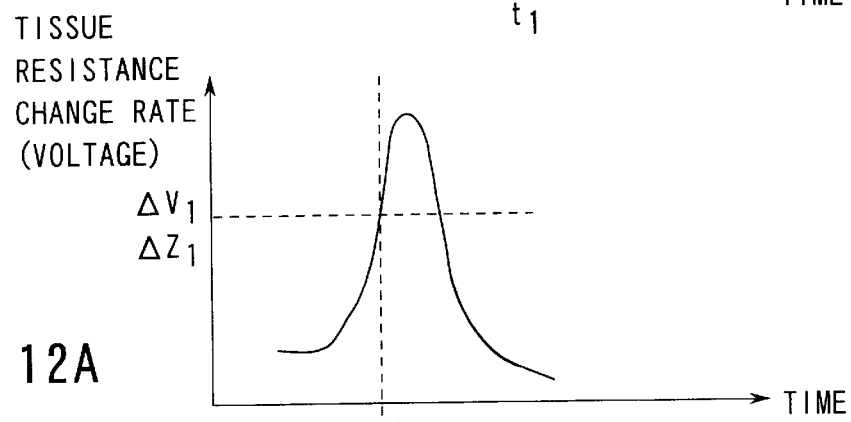
Figure 12B:
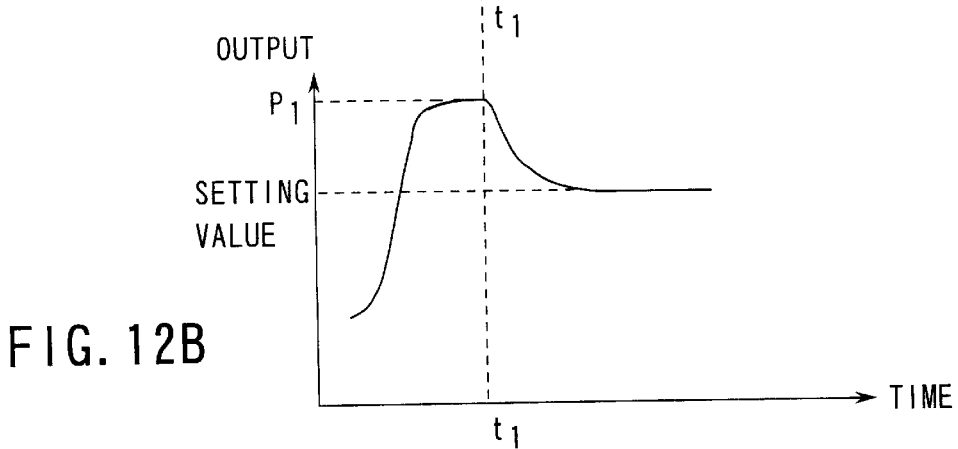

FIG. 12A is a characteristic graph showing a change rate of the tissue resistance or voltage, and FIG. 12B is a characteristic graph showing a time-based change of an actual output of the treatment tool.

After the output switch is turned, the high-frequency output increases and reaches a preset initial output value $P_1$. The tissue resistance and the voltage then increase. Further, it is detected that preset change rates $\Delta V_1$ and $\Delta Z_1$ of the resistance and voltage have been reached. At this time point (time $t_1$), stable cutting is enabled by the treatment tool. After the time $t_1$ has passed, the output of the treatment tool is reduced from the initial output value $P_1$ to a normal setting value.

Thus, according to the third embodiment, the electrode of the treatment tool can be distinguished by determining the time period from when the output switch is turned on to when the preset change rates $\Delta V_1$ and $\Delta Z_1$ of the resistance and voltage are obtained.

Next explanation will be made of a fourth embodiment of the present invention.

The electric surgical operation apparatus according to the fourth embodiment has the same schematic structure as that of the first embodiment shown in FIG. 4 previously explained, and explanation to the structure will be omitted herefrom.

Figures 13, 14:
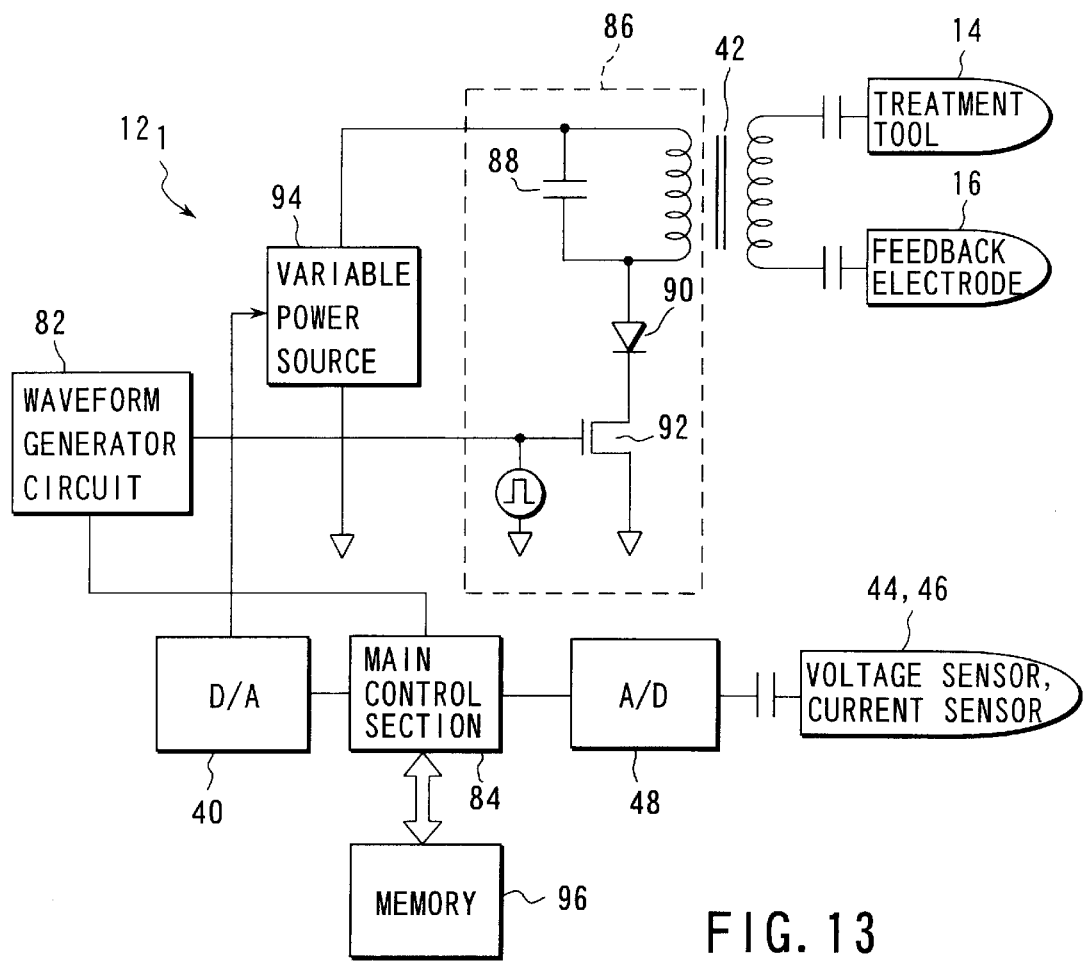
FIG. 13 is a block diagram showing a structure of a main part of a high-frequency cautery power source device according to the fourth embodiment of the present invention.
FIG. 14 explains output setting of the high-frequency cautery power source device in the fourth embodiment and shows an example of a table stored in a memory 96, expressing the relationship among setting outputs of the high-frequency cautery power source device, duties to the control signal of the parallel resonance amplifier, and amplifier supply voltages to the amplifier.

FIG. 13 is a block diagram showing a structure of a main part of a high-frequency cautery power source device according to the fourth embodiment of the present invention.

In FIG. 13, the waveform generator circuit 82 is connected to the main control section 84 and is also to a parallel resonance amplifier 86. The parallel resonance amplifier 86 is comprised of a resonance circuit constructed by a primary coil of an output transformer 42 and a capacitor 88, a diode 90, and a FET 92. Also, a secondary coil of the output transformer 42 is connected with a monopolar treatment tool 14 and a feedback electrode 16.

The resonance circuit constructed by the output transformer 42 and the capacitor 88 is connected with a variable power source 94 which supplies a voltage. Also, the main control section 84 is connected to the variable power source 94 through a D/A converter and to an A/D converter 48 and a memory 96 or the like which stores a supply voltage to the parallel resonance amplifier described later. The A/D converter 48 is connected with a voltage sensor 44 and a current sensor 46 described previously.

In the high-frequency cautery power source device 121 constructed as described above, a pulse-like waveform is outputted from a waveform generator circuit 82 and the FET 92 as a switching element is thereby switched on/off, so that a voltage is supplied to the parallel resonance circuit from the variable power source 94. As a result, a high-frequency current is supplied to the monopolar treatment tool 14 through the output transformer 42 and flows to the feedback electrode 16 through organic tissue not shown.

Also, signals detected by the voltage sensor 44 and the current sensor 46 are converted into digital signals by the A/D converter 48 and are then supplied to the main control section 84. Further, based on the signals detected by the voltage sensor 44 and the current sensor 46, the main control section 84 controls the voltage of the variable power source 94 through the D/A converter 40.

Next, output setting of the high-frequency cautery power source device $12_1$ of the fourth embodiment will be explained with reference to the FIGS. 14 and 15.

FIG. 14 shows an example of a table stored in the memory 96 and expresses the relationship among setting outputs of the high-frequency cautery power source device 12, duties to the control signal of the parallel resonance amplifier 86, and amplifier supply voltages to the amplifier. FIG. 15 is a chart which explains the duties to the control signal.

Figure 15:
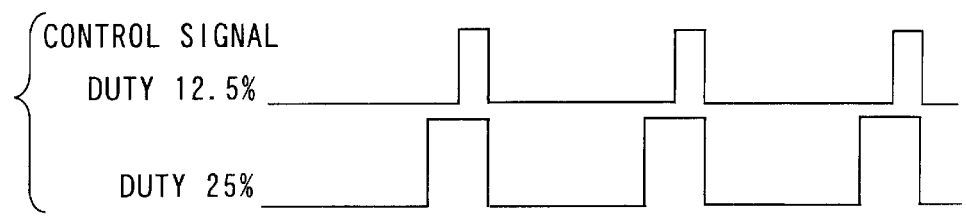
FIG. 15 explains the output setting of the high-frequency cautery power source device in the fourth embodiment and shows the duties to the control signal.

From FIGS. 14 and 15, if the setting outputs are 50 W, 100 W, and 150 W, the amplifier supply voltages are respectively 30V, 60V, and 90V. With respect to these setting outputs 50 W, 100 W, and 150 W, the duties to the control signal are each set to 12.5%.

If the setting outputs are 200 W, 250 W, and 300 W, the duties to the control signal are each set to 25.0% which is changed from 1.25%. With respect to these setting outputs 200 W, 250 W, and 300 W, the amplifier supply voltages are 60V, 75V, and 90V, respectively.

Thus, if the value of the setting output is low, a small duty to the control signal is set. When the supply voltage to the parallel resonance amplifier reaches a predetermined voltage, the duty is then set to a large value so that the supply voltage to the amplifier is decreased while the duty to the control signal is increased. Accordingly, the power source need not be have a large size but can be downsized. In addition, since the supply voltage to the amplifier can be reduced, a high-frequency leakage current can be reduced.

In the above embodiment, the duties to the control signal are not limited to 1.25% and 25.0% as long as the duties can be switched in relation to the setting outputs. Also, in the above embodiment, the small and large duties are respectively set to 1.25% and 25.0%. However, for example, if the first setting output is 200 W, the small and large duties can be changed to 25.0% and more in accordance with the setting.

Next, a fifth embodiment of the present invention will be explained.

Figure 16:
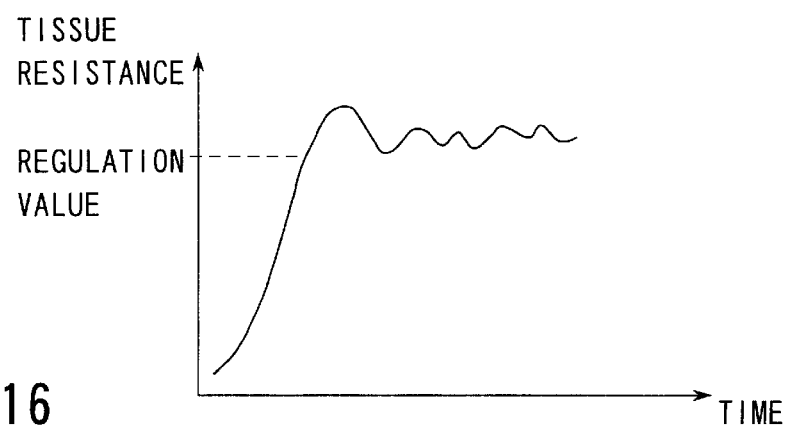
FIG. 16 explains a fifth embodiment of the present invention and is a characteristic graph showing a time-based change of the tissue resistance.

FIG. 16 is a characteristic graph showing a time-based change of the tissue resistance.

After the output switch is turned, the tissue resistance of organic tissue which the monopolar treatment tool 14 contacts increases. When the value of the tissue resistance reaches a preset regulation value, the duty to the control signal is then changed to a large value.

Figure 17:
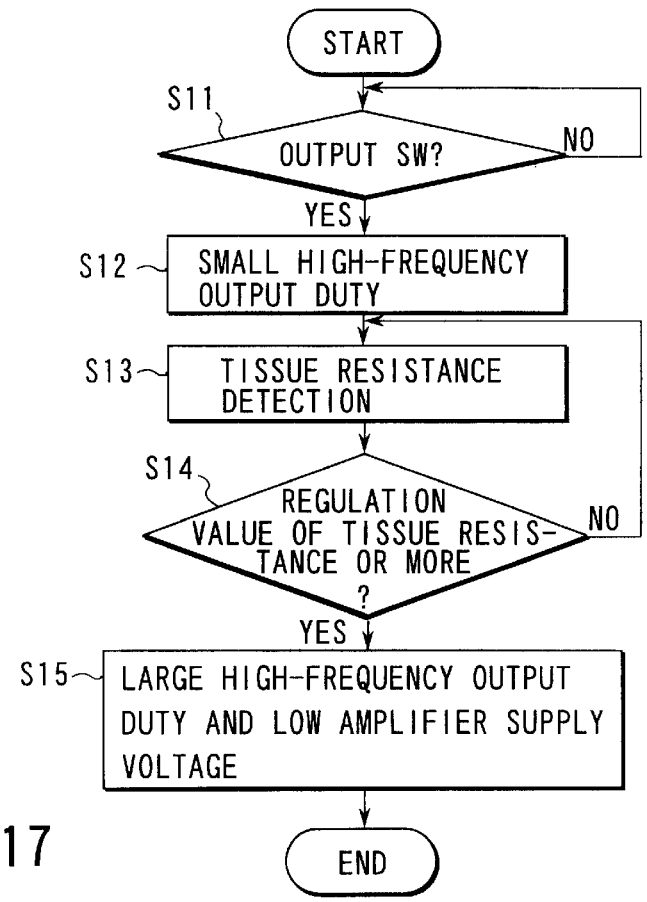
FIG. 17 is a flowchart which explains operation of the fifth embodiment.

FIG. 17 is a flowchart which explains the operation of the fifth embodiment.

At first, in a step S11, whether or not a switch for a high-frequency output which is the foot switch 18 is on is determined. If the foot switch 18 is on, a high-frequency output is supplied to the monopolar treatment tool 14 in a subsequent step S12. In this case, the duty is set to a small value at first, e.g., 12.5%.

Subsequently, in a step S13, the tissue resistance of organic tissue which the monopolar treatment tool 14 contacts is detected through a voltage sensor 44 and a current sensor 46. Further, in a step S14, whether or not the value of the tissue resistance is equal to or mover than a regulation value is determined.

If the tissue resistance does not yet reach the regulation value, the flow returns to the step S13, and a high-frequency output is supplied with the duty kept small. In this case, for example, with respect to a high-frequency output up to 150 W, the duty to the control signal is 12.5% and the supply voltage from the variable power source 94 is 90V at most.

If the value of the tissue resistance is equal to or more than the regulation value in the step S14, the flow goes to a step S15. The duty of the high-frequency output supplied is then switched to a large value of 25.0%, for example. At this time, if the setting output is 200 W or more, the duty to the control signal is switched from 12.5% to 25.0%, and simultaneously, the supply voltage from the variable power source 94 decreases to 60V from 90V which is used for 150 W. Thereafter, if the setting output increases, the supply voltage of the variable power source 94 also increases.

By thus switching the duty to the control signal in accordance with the tissue resistance of organic tissue, it is possible to reduce the supply voltage to the parallel resonance amplifier while using a large setting output. Accordingly, the power source can be downsized. As a result of this, a high-frequency leakage current can be reduced.

In the embodiment described above, the duties to the control signals are not limited to 12.5% and 25.0as long as the duties can be switched in accordance with the setting output. Also, in the above embodiment, the small duty in the step S12 and the large duty in the step S15 are respectively set to 12.5% and 25.0. However, for example, if the first setting output is set to 200 W, the small and large duties can be respectively changed to 25.0% and more in accordance with the setting.

Figure 18:
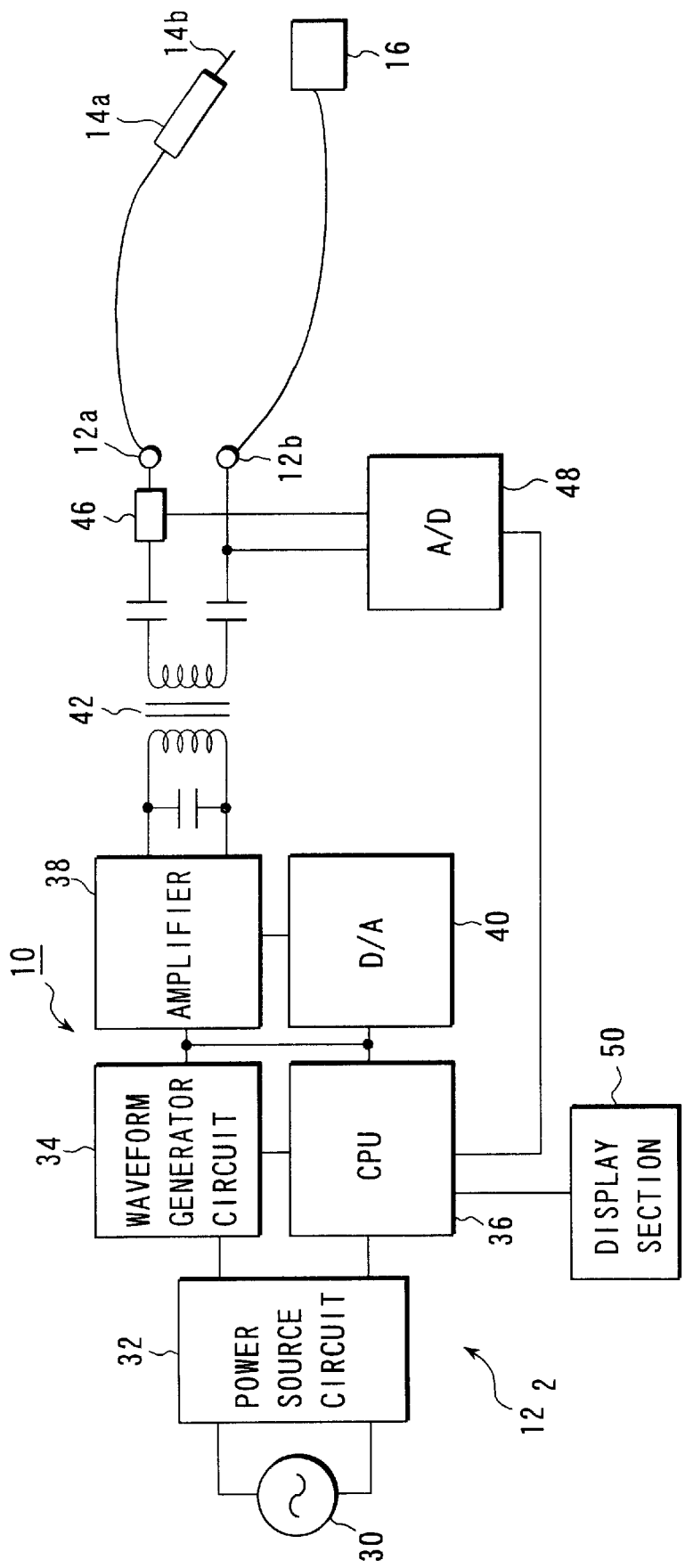
FIG. 18 is a view showing a schematic structure of an electric surgical operation apparatus according to a sixth embodiment of the present invention.

FIG. 18 is a view showing a schematic structure of an electric surgical operation apparatus according to a sixth embodiment of the present invention.

The high-frequency cautery power source device $12_2$ according to the sixth embodiment differs from the high-frequency cautery power source device of the first embodiment only in that the voltage sensor 44 is removed from the structure shown in FIG. 5A. The other points of the structure are the same as those of the structure according to the first embodiment, and therefore, explanation thereof will be omitted herefrom.

FIGS. 19 explain feedback control. FIG. 19A is a characteristic graph showing time-based changes of the voltage applied to organic tissue, the current, and the resistance of tissue. FIG. 19B is a characteristic graph showing a time-based change of an actually supplied power.

At first, a high-frequency output is supplied and the tissue resistance then increases. As the tissue resistance increases, the output voltage increases. In contrast, the output current then decreases.

After predetermined regulation values, e.g., a regulation resistance value, a regulation voltage value, and a regulation current value are reached at a time point $t_{11}$, the actual output is lowered and the supply of the power is limited, as shown in FIG. 19B.

FIGS. 20A through 20C shows waveforms of the output voltage described above.

FIG. 20A shows a waveform 1 at a peak value $V_{PP1}$. FIG. 20B shows a waveform 2 at a peak value $V_{PP2}$ having higher tissue impedance than the waveform 1. FIG. 20C shows a waveform 3 at a peak value $V_{PP3}$ having much higher tissue impedance than the waveform 2. The values of crest factors are in the order of waveform 1>waveform 2>waveform 3 from the highest value.

Further, the output voltage is outputted at first in the form of the waveform 2 shown in FIG. 20A. Next, the waveform 2 shown in FIG. 20B is outputted. Further, the waveform 3 shown in FIG. 20C is outputted then.

Of the waveforms 1 to 3, the waveform 1 has a substantially pulse-wave-like shape and has a high crest factor, so a high coagulation function is obtained. However, this waveform has a high peak value and the voltage is therefore high, so a spark occurs and tissue is broken. The waveform 2 has a lower crest factor than the waveform 1 but has a broadened pulse width although the peak value is low. The waveform 3 has a lower peak value but has a much broader pulse width, so the waveform has a sine-wave-like shape. Therefore, the voltage value can be sufficiently suppressed. By this setting, the waveforms 1 and 2 are capable of supplying a substantially equal power.

As described previously, the output voltage increases as the tissue resistance increases. If a waveform having a large crest factor is used, the output voltage must be large. Then, a problem arises in that the high-frequency leakage current increases as the load to the power source increases and the output voltage increases.

Therefore, if, starting from the output based on the waveform 1, the waveform 1 is switched to the waveform 2 and then to the waveform 3 to lower the peak value of the waveform so that the crest factor is lowered, the output voltage then need not be increased. As a result, the load to the power source, noise, and increase of the leakage current can be prevented.

In this case, every of the waveforms 1, 2, and 3 is used for coagulation. In particular, although the sine wave of the waveform 3 is conventionally used only for incision, this waveform can be used as an output for coagulation by setting the output voltage to be equal to or lower than the voltage at which a spark discharge (arc discharge) is caused.

Figure 21:
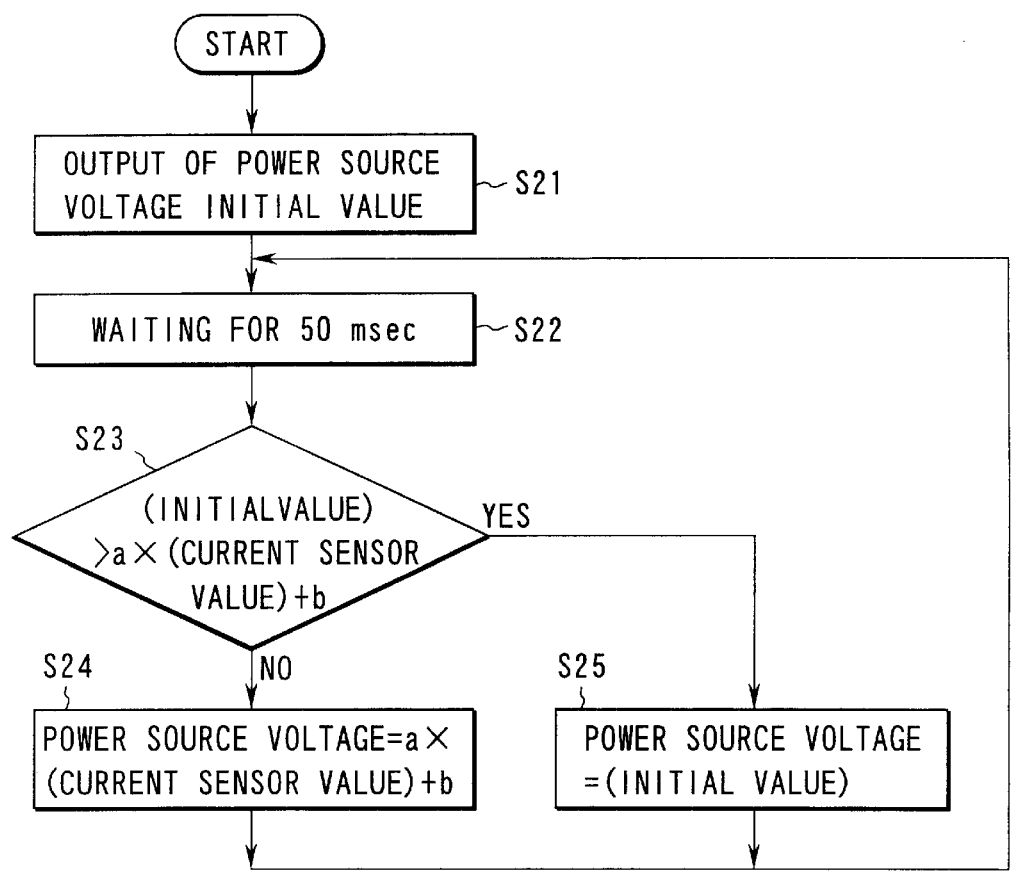
FIG. 21 is a flowchart which explains operation of the sixth embodiment of the present invention.

Next, operation of the sixth embodiment of the present invention will be explained with reference to the flowchart in FIG. 21.

At first, a power source voltage is outputted at an initial value in a step S21 after the operation is started. At this time, a power source voltage according to the setting is outputted. Further, in a step S22, the apparatus waits for a predetermined time, e.g., 50 msec. In a step S23, the initial power source voltage value and a calculation value of a present current (which is expressed as a×(current sensor value)+b in this case) are compared with each other.

Figure 22:
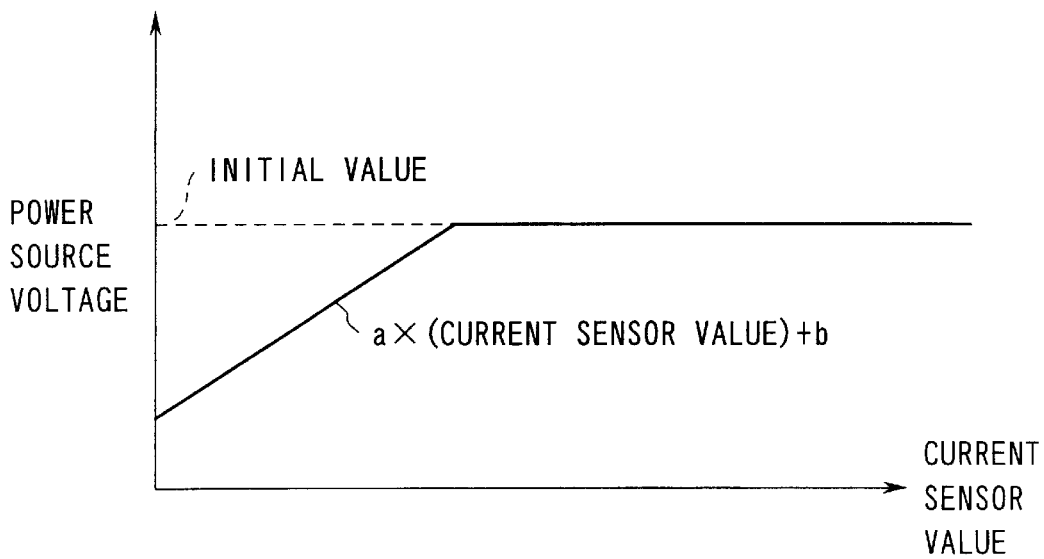
FIG. 22 is a characteristic graph showing a relationship between the power source voltage for controlling the output voltage and the value of a current sensor.

FIG. 22 is a characteristic graph showing a relationship between the power source voltage for controlling the output voltage and the value of the current sensor 46.

Conventionally, as indicated by a broken line in the figure, the power source voltage is constant at a predetermined setting value regardless of the current sensor value. In contrast, in the sixth embodiment of the present invention, the value of the power source voltage is changed from an initial value to a predetermined setting value, as indicated by a continuous line. That is, the power source voltage is dropped from a predetermined setting value when the current sensor value is decreased, i.e., the value of the tissue resistance is increased. In this manner, the output power is decreased. Further, from the predetermined setting value as a boundary, supply of a flat power source voltage is started.

If the calculation value is higher than the initial value in the step S23, i.e., if the impedance is high, the flow goes to the step S24. Further, in the step S24, the power source voltage is set to the calculation value and is decreased as shown in FIG. 22.

Meanwhile, if the initial value is higher than the calculation value in the step S23, i.e., if the impedance is low, the flow goes to a step S25. Further, in this step S25, the initial value is directly outputted as the power source voltage.

Figure 23:
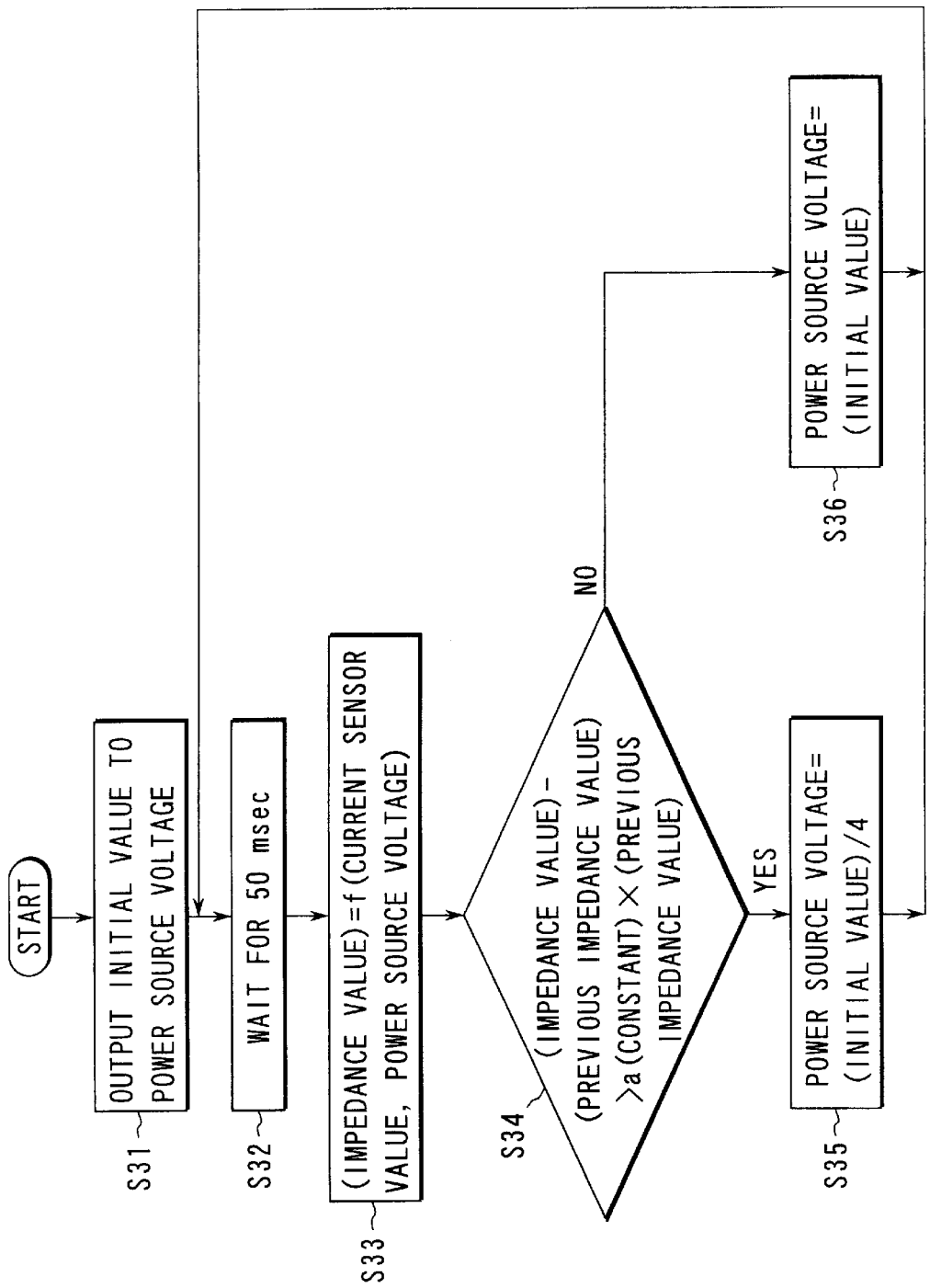
FIG. 23 is a flowchart which explains operation of a modification example of the sixth embodiment of the present invention.

Next, a modification of the sixth embodiment will be explained with reference to the flowchart in FIG. 23.

After operation is started, at first, the power source voltage is outputted at the initial value in the step S31.

Subsequently, in a step S32, the apparatus waits for a predetermined time, e.g., 50 msec. Further, in a step S33, an impedance value is obtained. The output impedance can also be obtained from the current sensor value and the value of output voltage/(power source voltage×turn ratio) since the output voltage in the secondary side is determined, for example, by the turn ratio of the coil of the output transformer. Further, a table showing values of the current sensor and setting values may be stored in a storage means, and the impedance may be obtained by reading the table.

Next, in a step S34, whether or not the change of the impedance is larger than a predetermined value is determined. That is, the difference between a present impedance value and a previous impedance value is larger than a value obtained by multiplying the previous impedance value by a predetermined constant.

If the change of the impedance is larger than the predetermined value, the flow goes to a step S35. Further, in this step S35, the power source voltage is set to a value obtained by dividing the initial value by a certain value, e.g., 4. Otherwise, if the change of the impedance is smaller than the predetermined value, the flow goes to a step S36, and the power source voltage is kept set at the initial value.

Explained next will be a seventh embodiment of the present invention.

Figure 24:
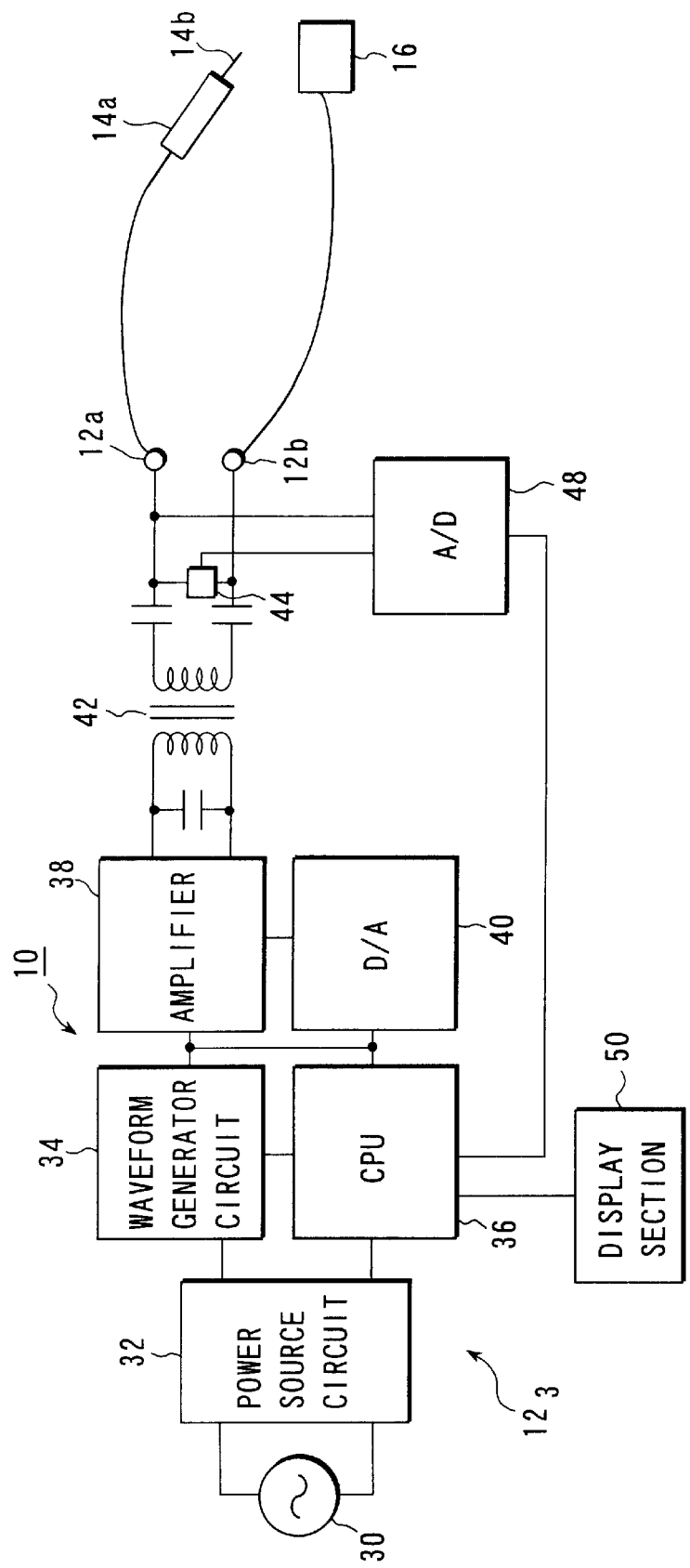
FIG. 24 is a view showing the internal structure of a high-frequency cautery power source device according to a seventh embodiment of the present invention.

FIG. 24 is a view showing the internal structure of a high-frequency cautery power source device according to the seventh embodiment of the present invention.

In the sixth embodiment described above, the output voltage is detected by a current sensor. However, in the seventh embodiment, a voltage sensor is provided in place of the current sensor. That is, the output transformer 42 is connected, in its secondary side, to terminals 12a and 12b through a capacitor and a voltage sensor 44. The other points of the structure of the high-frequency cautery power source device 123 are the same as those of the sixth embodiment shown in FIG. 18, and therefore, explanation thereof will be omitted herefrom.

Figure 25:
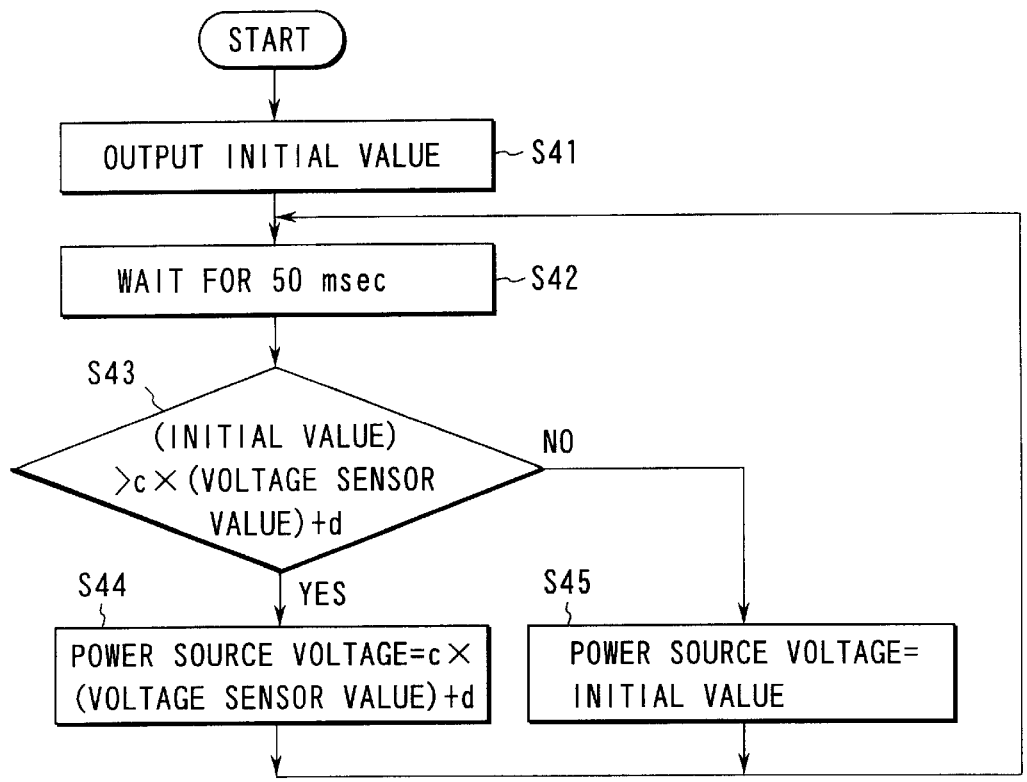
FIG. 25 is a flowchart which explains operation of the seventh embodiment.

FIG. 25 is a flowchart which explains the operation of the seventh embodiment. This operation is basically similar to that of the sixth embodiment shown in FIG. 21.

After the operation is started, at first, a power source voltage is outputted at an initial value in a step S21. Subsequently, in a step S22, the apparatus waits for a predetermined time, e.g., 50 msec. Then, in a step S23, the initial power source voltage value and a calculation value of a present voltage (which is expressed as c×(voltage sensor value)+d in this case) are compared with each other.

Figure 26:
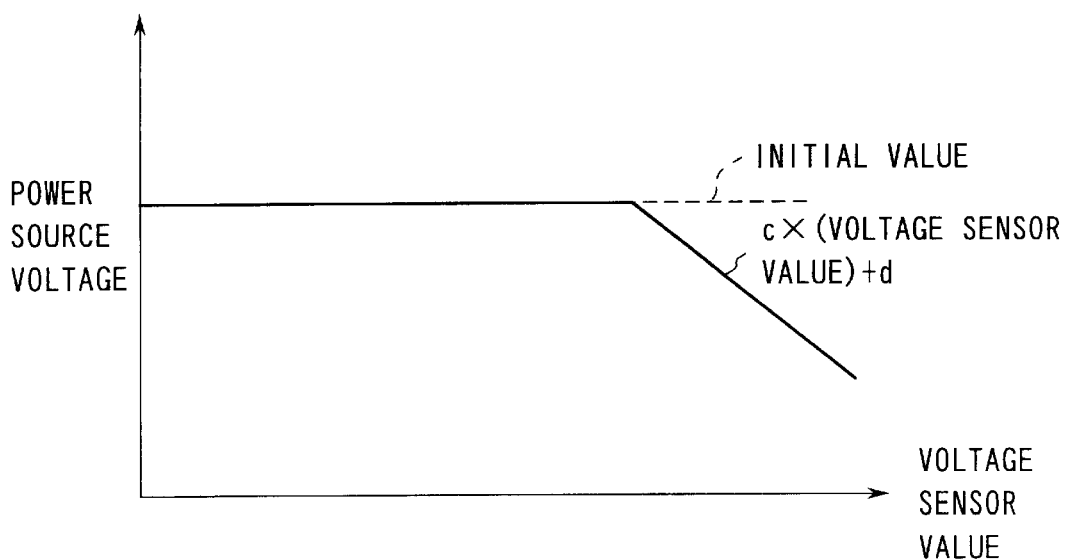
FIG. 26 is a characteristic graph showing a relationship between the power source voltage for controlling the output voltage and the value of a voltage sensor.

FIG. 26 is a characteristic graph showing a relationship between the power source voltage for controlling the output voltage and the value of the voltage sensor 44.

Conventionally, as indicated by a broken line in the figure, the power source voltage is constant at a predetermined setting value regardless of the voltage sensor value. In contrast, in the second embodiment, the value of the power source voltage is constant from an initial value to a predetermined setting value, and the value of the power source voltage which exceeds the predetermined setting value is also changed, as indicated by a continuous line. That is, the power source voltage is dropped from a predetermined setting value when the voltage sensor value is increased. In this manner, the output power is decreased. Further, from the predetermined setting value as a boundary, supply of a flat power source voltage is started.

If the calculation value is higher than the initial value in the step S43, i.e., if the impedance is high, the flow goes to the step S44. Further, in the step S44, the power source voltage is set to the calculation value and is decreased as shown in FIG. 26.

Meanwhile, if the initial value is higher than the calculation value in the step S43, i.e., if the impedance is low, the flow goes to a step S45. Further, in this step S45, the initial value is directly outputted as the power source voltage.

As has been described above, according to the present invention, it is possible to provide an electric surgical operation apparatus capable of shortening easily and securely the rising time until an incision effect or a coagulation effect appears, so that cutting sharpness is improved, the operation time is shortened, and the safety is improved, even if electrodes having different volumes or surface areas are used for the treatment tool.

Also, it is possible to provide an electric surgical operation apparatus which does not complicate its structure nor increase costs.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of controlling an electric surgical operation apparatus for treating a living body using high-frequency energy, comprising:

a first step of detecting whether or not a treatment unit is in contact with the living body on the basis of a physical quantity of the high-frequency energy supplied to the treatment unit;

a second step of bringing a high-frequency energy generating circuit that supplies the high-frequency energy to the treatment unit so as to have a first operating state in which the high frequency energy generating circuit is enabled to supply first high-frequency energy increasing a temperature of the treatment unit to a temperature that allows the treatment unit to treat the living body, in case the result of the first step is that the treatment unit is in contact with the living body;

a third step of determining whether or not the temperature of the treatment unit has increased enough to treat the living body by means of said first high-frequency energy generated by the high-frequency energy generating circuit on the basis of the physical quantity of the high-frequency energy supplied to the treatment unit; and a fourth step of changing a setting of the high-frequency energy generating circuit so as to have a second operating state in which the high-frequency energy generating circuit is enabled to supply second high-frequency energy which is lower than the first high-frequency energy and which allows the high-frequency energy generating circuit to treat the living body, in case the temperature of the treatment unit has increased enough to treat the living body in the third step.

2. A method according to claim 1, wherein the first step, the second step, the third step and the fourth step are carried out in order.

3. A method according to claim 1, wherein the second step sets an amount of electricity output from the high-frequency energy generating circuit.

4. A method according to claim 1, wherein the second step sets a waveform output from the high-frequency energy generating circuit.

5. A method according to claim 4, wherein the second step sets a duty of the waveform.

6. A method according to claim 1, wherein the treatment unit is exchangeable and the second step sets the high-frequency energy generating circuit according to the exchangeable treatment unit.

7. A method according to claim 6, wherein the second step sets an amount of electricity output from the high-frequency energy generating circuit.

8. A method according to claim 6, wherein the second step sets a waveform output from the high-frequency energy generating circuit.

9. An electric surgical operation apparatus for treating a living body using high-frequency energy, comprising:

a high-frequency energy generating circuit which generates the high-frequency energy;

a treatment unit which treats the living body by using the high-frequency energy generated in the high-frequency energy generating circuit;

a detection circuit which detects a physical quantity of the high-frequency energy supplied to the treatment unit from the high-frequency energy generating circuit; and a control circuit which controls the high-frequency energy generating circuit on the basis of detection signals output from the detection circuit, wherein the control circuit includes a first processing function of determining whether the treatment unit is in contact with the living body or not, on the basis of the physical quantity of the high-frequency energy, a second processing function of outputting a first setting signal to the high-frequency energy generating circuit in case the result of the first processing function is that the treatment unit is in contact with the living body, the first setting signal bringing a high-frequency energy generating circuit to a first operating state in which the high-frequency energy generating circuit supplies first high-frequency energy which is effective in increasing a temperature that allows the treatment unit to treat the living body, a third processing function of determining whether or not the temperature of the treatment unit has increased enough to treat the living body by means of said first high-frequency energy generated by the high-frequency energy generating circuit on the basis of the physical quantity of the high-frequency energy detected by the detection circuit, and a fourth processing function of changing the first setting signal to a second setting signal in case the temperature of the treatment unit has increased enough to treat the living body in the third processing function, the second setting signal supplying second high-frequency energy which is effective in treating the living body and lower than the first high-frequency energy.

10. An electric surgical operation apparatus according to claim 9, wherein the control circuit performs the first function, the second function, the third function and the fourth function in order.

11. An electric surgical operation apparatus according to claim 9, wherein the high-frequency energy generating circuit changes an amount of electricity the high-frequency energy generating circuit outputs, based on the first setting signal output from the control circuit when the second function of the control unit is performed.

12. An electric surgical operation apparatus according to claim 9, wherein the high-frequency energy generating circuit changes a waveform the high-frequency energy generating circuit outputs, based on the first setting signal output from the control circuit when the second function of the control unit is performed.

13. An electric surgical operation apparatus according to claim 9, wherein the high-frequency energy generating circuit changes a duty of the waveform the high-frequency energy generating circuit outputs, based on the first setting signal output from the control unit when the second function of the control unit is performed.

14. An electric surgical operation apparatus according to claim 9, wherein the physical quantity detected by the detection circuit is at least one of current and voltage.

15. An electric surgical operation apparatus according to claim 9, wherein the control unit has an operation button that changes the first setting signal output from the control circuit when the second function of the control unit is performed.

16. An electric surgical operation apparatus according to claim 9, wherein the control unit has an operation button that changes the second setting signal output from the control circuit when the fourth function of the control unit is performed.

17. An electric surgical operation apparatus according to claim 9, wherein the treatment unit is exchangeable and the second function of the control unit is to output the first setting signal according to the exchangeable treatment unit.

18. An electric surgical operation apparatus according to claim 17, wherein the physical quantity detected by the detection circuit is at least one of current and voltage.

19. An electric surgical operation apparatus according to claim 17, wherein the high-frequency energy generating circuit sets an amount of electricity the high-frequency energy generating circuit outputs, based on the first setting signal output from the control unit when the second function of the control unit is performed.

20. An electric surgical operation apparatus according to claim 17, wherein the high-frequency energy generating circuit sets a waveform the high-frequency energy generating circuit outputs, based on the first setting signal output from the control unit when the second function of the control unit is performed.

21. An electric surgical operation apparatus according to claim 17, wherein the high-frequency energy generating circuit sets a duty of the waveform the high-frequency energy generating circuit outputs, based on the first setting signal output from the control unit when the second function of the control unit is performed.

22. An electric surgical operation apparatus according to claim 21, wherein the control unit further comprises a storage unit in which the duty of the waveform is stored beforehand and outputs a setting signal according to the duty of the waveform stored in the storage unit.

23. An electric surgical operation apparatus according to claim 17, wherein the third function of the control unit is to determine whether or not the temperature of the treatment unit is increased to a temperature high enough to treat the living body, based on a calculation using at least one of impedance and resistance as a parameter.

24. An electric surgical operation apparatus according to claim 17, wherein the control unit determines a type of the exchangeable treatment unit, based on the detection signal output from the detection circuit.

* * * * *